United States Patent
Martin et al.

(10) Patent No.: US 9,924,998 B2
(45) Date of Patent: Mar. 27, 2018

(54) ABLATION SYSTEM, CLAMP AND METHOD OF USE

(75) Inventors: Keith Edward Martin, Mason, OH (US); Salvatore Privitera, Mason, OH (US)

(73) Assignee: AtriCure, Inc., Mason, OH (US)

( * ) Notice: Subject to any disclaimer, the term of this patent is extended or adjusted under 35 U.S.C. 154(b) by 2126 days.

(21) Appl. No.: 11/970,005

(22) Filed: Jan. 7, 2008

(65) Prior Publication Data

US 2008/0172048 A1 Jul. 17, 2008

Related U.S. Application Data

(60) Provisional application No. 60/884,783, filed on Jan. 12, 2007, provisional application No. 60/884,719, filed on Jan. 12, 2007.

(51) Int. Cl.

| A61B 18/14 | (2006.01) |
| A61B 18/12 | (2006.01) |
| A61B 18/04 | (2006.01) |
| A61B 18/18 | (2006.01) |
| A61B 17/29 | (2006.01) |
| A61B 18/00 | (2006.01) |

(52) U.S. Cl.
CPC ...... *A61B 18/1442* (2013.01); *A61B 18/1447* (2013.01); *A61B 18/18* (2013.01); *A61B 2017/2945* (2013.01); *A61B 2018/00702* (2013.01); *A61B 2018/00791* (2013.01); *A61B 2018/00875* (2013.01); *A61B 2018/124* (2013.01); *A61B 2018/145* (2013.01); *A61B 2018/1432* (2013.01); *A61B 2018/1467* (2013.01)

(58) Field of Classification Search
USPC .............................. 606/41, 50–52, 205–207
See application file for complete search history.

(56) References Cited

U.S. PATENT DOCUMENTS

| 2,031,682 | A | | 2/1936 | Wappler et al. | |
| 5,443,463 | A | * | 8/1995 | Stern et al. | 606/51 |
| 5,688,270 | A | | 11/1997 | Yates et al. | |
| 5,700,261 | A | * | 12/1997 | Brinkerhoff | 606/41 |
| 5,755,717 | A | | 5/1998 | Yates et al. | |
| 6,059,778 | A | * | 5/2000 | Sherman | 606/34 |

(Continued)

OTHER PUBLICATIONS

European Patent Office Search Report for EP 08 25 0153 dated Mar. 31, 2008.

*Primary Examiner* — Ronald Hupczey, Jr.
(74) *Attorney, Agent, or Firm* — Willis IP; Ryan Willis

(57) ABSTRACT

A method and apparatus for ablating tissue are disclosed that comprise positioning two or more bidirectional ablation energy sources in spaced-apart relation in sufficient proximity to the tissue to be ablated so that, upon activation each energy source creates an energy field in the tissue to be ablated. The energy sources are spaced such that the energy fields created by at least one of the activated sources partially overlaps with the energy field created by one or more of the other energy sources. The energy sources are alternately activated and deactivated, so that a substantially constant energy field results where the energy fields created by at least two of the energy sources overlap. While the energy sources are preferably RF energy sources, other energy sources, such as microwave, may be used.

35 Claims, 3 Drawing Sheets

(56) References Cited

U.S. PATENT DOCUMENTS

| | | |
|---|---|---|
| 6,086,586 A | 7/2000 | Hooven |
| 6,152,923 A * | 11/2000 | Ryan ............................... 606/51 |
| 6,156,060 A | 12/2000 | Roy et al. |
| 6,162,220 A | 12/2000 | Nezhat |
| 6,413,253 B1 | 7/2002 | Koop et al. |
| 6,629,535 B2 | 10/2003 | Ingle et al. |
| 6,802,843 B2 | 10/2004 | Truckai et al. |
| 6,918,906 B2 | 7/2005 | Long |
| 7,022,121 B2 | 4/2006 | Stern et al. |
| 2001/0008967 A1* | 7/2001 | Sherman ......................... 606/34 |
| 2002/0091384 A1* | 7/2002 | Hooven et al. ................ 606/41 |
| 2002/0156472 A1* | 10/2002 | Lee et al. ........................ 606/41 |
| 2004/0039429 A1* | 2/2004 | Daniel et al. ................. 607/100 |
| 2004/0068274 A1* | 4/2004 | Hooven ......................... 606/151 |
| 2004/0143263 A1* | 7/2004 | Schechter et al. ............. 606/51 |
| 2005/0090815 A1* | 4/2005 | Francischelli et al. ........ 606/32 |
| 2006/0015095 A1* | 1/2006 | Desinger et al. .............. 606/41 |
| 2007/0088347 A1* | 4/2007 | Young et al. .................. 606/41 |

\* cited by examiner

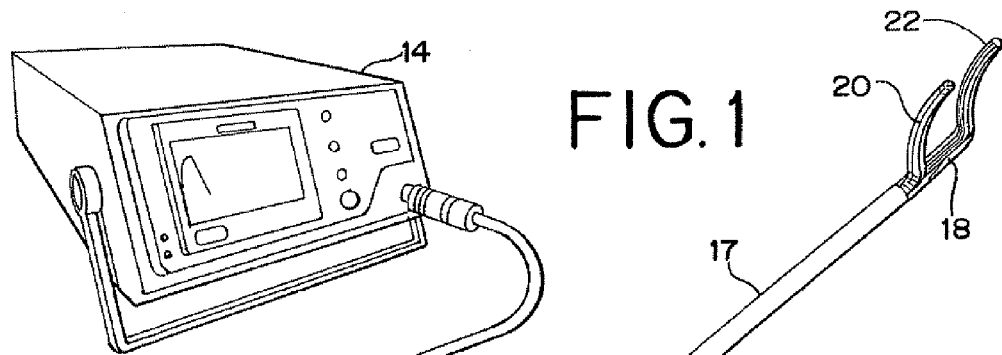
FIG. 1
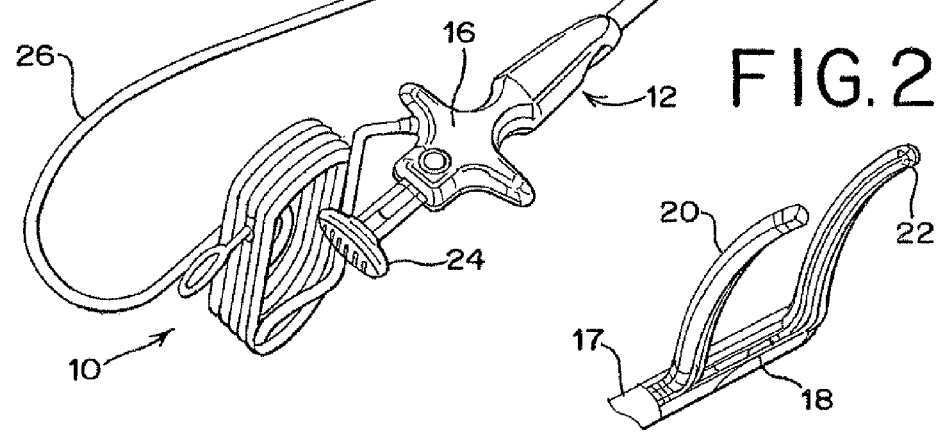
FIG. 2
FIG. 3
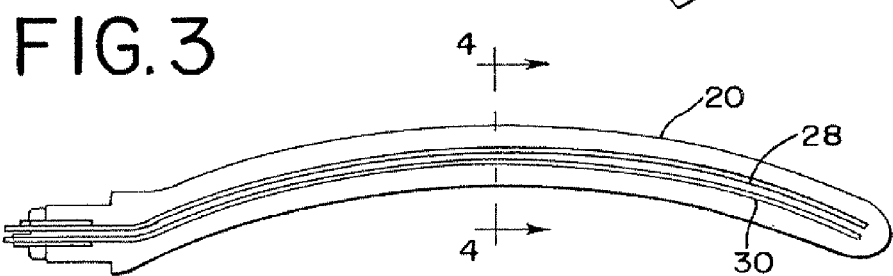
FIG. 4
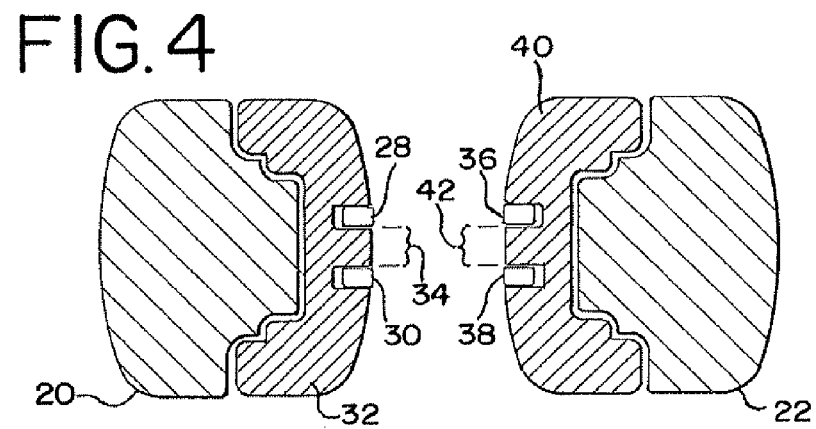

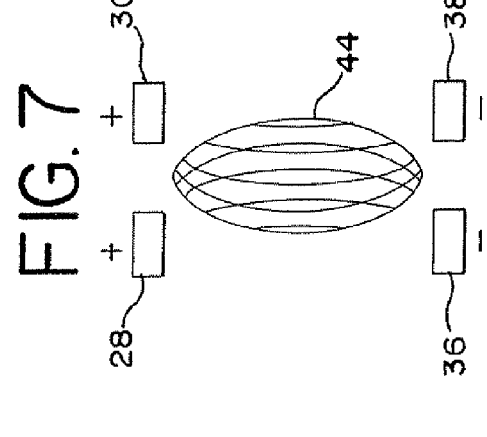
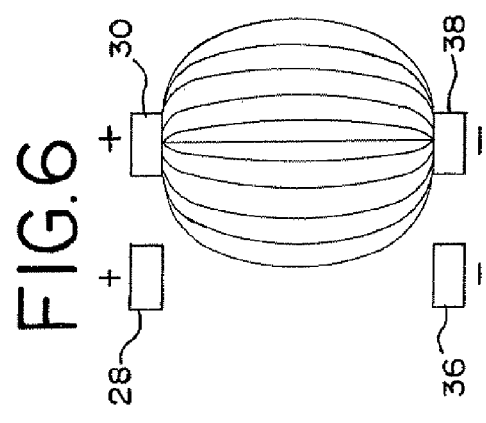
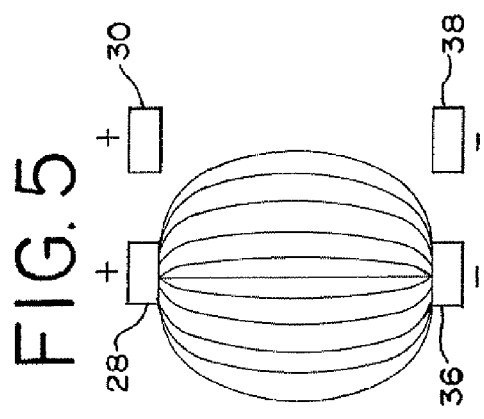
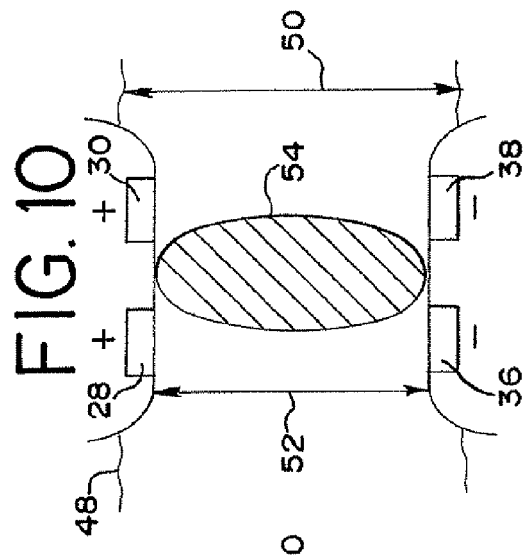
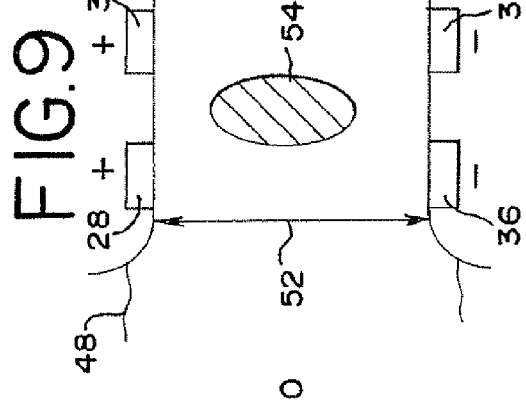
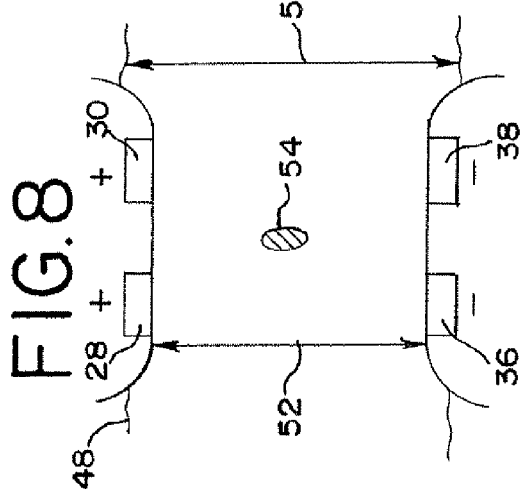

ABLATION SYSTEM, CLAMP AND METHOD OF USE

CROSS REFERENCE TO RELATED APPLICATION

This application claims the benefit of U.S. Provisional Application Ser. No. 60/884,783, filed Jan. 12, 2007 and is related to U.S. Provisional Application Ser. No. 60/884,719, filed Jan. 12, 2007, both of which are incorporated by reference in their entirety.

FIELD OF THE INVENTION

The present invention relates, in general, to methods and apparatus for tissue ablation instrument and, more particularly, to devices, systems and methods using resistive and thermal heating for the ablation of tissue.

BACKGROUND OF THE INVENTION

It is known to use bipolar RF energy devices that clamp tissue between opposed electrodes and apply RF energy to heat tissue to form lines of ablation on the tissue. This has found particular application in the formation of strategically located lines of ablation in cardiac tissue to block spurious electrical signals to the heart, which has been particularly beneficial in the treatment of atrial fibrillation. See, e.g., U.S. Pat. No. 6,889,694 which is incorporated herein by reference.

Such bipolar electrode devices apply energy directly to the surface of tissue clamped between a first electrode and a second electrode. The first electrode, the clamped tissue, and the second electrode form a conductive resistive circuit. As the moisture in the tissue conducts the RF energy, the tissue begins to desiccate. As the tissue desiccates it becomes more resistive. The application of bipolar RF energy on tissue shows that tissue desiccation progresses inwardly from the outside or surface of the tissue near the electrode-tissue contact area, where the current flux or density is greatest. Surface desiccation increases resistance in the tissue and can make it more difficult to achieve good depth of penetration in underlying tissue without creating a larger than desired area of ablated tissue or excessive surface heating adjacent to the electrodes. A recent study reported that to achieve a depth of ablation of 5 mm, a width of ablation of almost 8 mm wide in the endocardium resulted. See, "Mechanism, Localization, and Cure of Atrial Arrhythmias Occurring After a New Intraoperative Endocardial Radiofrequency Ablation Procedure for Atrial Fibrillation," Thomas, et al., *Journal of the American College of Cardiology*, Vol. 35, No. 2, 2000, hereby incorporated by reference. While a wider ablation facilitates the surgeon's visual confirmation that an ablation has been created, it is still desirable to control the width of ablation so as to keep the width of the ablation and thermal spread from the zone of ablation within certain limits so as to not irreversibly damage more cardiac tissue than necessary.

To overcome surface tissue heating effects, techniques such as cooling or cryogenics have been used, and selected positioning of the electrodes has been considered. See, for example, U.S. Pat. No. 6,413,253 to Koop et al., U.S. Pat. No. 6,629,535 to Ingle et al., and U.S. Pat. No. 7,022,121 to Stern et al. and U.S. Pat. No. 6,918,906 to Long.

Consequently, a significant need exists for an improved electrosurgical device and method of use that can enhance lesion formation and provide for more efficient ablation.

BRIEF SUMMARY OF THE INVENTION

The invention provides for an, apparatus and system for ablating tissue, along with a method of use, that comprises an energy generator and a plurality of ablation energy sources that are adapted to be positioned in proximity to the tissue to be ablated. Each energy source is in operative communication with the generator, and each source, when activated, generates an energy field that at least partially overlaps with an energy field created by one or more of the other sources. A control system is provided that is operatively associated with both the generator and the sources to alternately activate and deactivate the sources so that a substantially constant energy field is created in the area of overlap.

More specifically, and without limiting the foregoing, a method of tissue ablation using RF electrodes is provided in which the tissue to be ablated is contacted with a plurality of electrode pairs, the electrodes of each pair being of opposite RF energy polarity so as to provide a current flux between the members of each pair when activated. The electrode pairs are then alternately activated and deactivated with RF energy to create at least one zone of primary heating in the tissue that is spaced from or substantially non-coincident with at least one zone of the highest current flux in the tissue. This is unlike the prior art devices where the zones of primary heating and highest current density substantially coincide or contained in the same space and are located at the electrode-tissue interface.

In another aspect of invention, a tissue ablation method is provided that comprises positioning two or more preferably bi-directional ablation energy sources in spaced-apart relation in sufficient proximity to the tissue to be ablated so that, upon activation each energy source creates an energy field in the tissue to be ablated. The energy sources are spaced such that the energy fields created by at least one of the activated sources partially overlaps with the energy field created by one or more of the other energy sources. The energy sources are alternately activated and deactivated, so that a substantially constant energy field results where the energy fields created by at least two of the energy sources overlap. While the energy sources are preferably RF energy sources, other energy sources, such as microwave, ultrasound (especially High Intensity Focused Ultrasound or HIFU), laser etc. may be used.

More specifically, a tissue ablation apparatus is provided that comprises opposed relatively moveable jaws for clamping the tissue to be ablated therebetween. A plurality of electrode pairs is provided, one electrode of each pair being carried on one jaw and being adapted to be connected to one terminal of an RF generator, and the other electrode of each pair being carried on the other jaw and being adapted to be connected to the opposite terminal of an RF generator. A current flux is created between the respective electrodes of each pair when activated by the generator. The electrode pairs are located on the jaws such that when alternately activated and deactivated by and RF generator, the electrodes create at least one flux zone of primary heating in the tissue that is spaced from at least one flux zone of the highest current flux in the tissue.

In another aspect of the invention, the method can be practiced, and the device can be provided, with multiple pairs of energy sources or electrodes. For example, if two pairs are provided, one zone of overlap results, if three pairs are provided, two zones of overlap result, if four pairs are provided, three zones of overlap result etc. The number of pairs of energy sources can be selected to provide an ablation line, area or zone of the desired width.

In another aspect of the invention, sufficient pressure is applied to the tissue to be ablated to reduce its moisture content, and also to normalize the impedance within the tissue and to provide good contact between the electrodes and the tissue to normalize the electrode to tissue impedance. Preferably, the pressure applied to the tissue is proportional to its thickness, i.e. increasing pressure with increasing tissue thickness. This pressure may be the result of clamping force, suction, or other means.

In another aspect, the method and device may utilize impedance and/or temperature sensors to control the energy delivered to the instrument.

These and other aspects and advantages of the present invention will become apparent from the accompanying drawings and the following detailed description.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 1 is a perspective view of a system according to the present invention including an RF energy generator and a cardiac ablation clamp having opposed jaws.

FIG. 2 is an enlarged fragmentary perspective view of the opposed jaws of the ablation clamp shown in FIG. 1.

FIG. 3 is a plan view of one of the jaws of the ablation clamp of FIG. 1.

FIG. 4 is an enlarged cross-sectional view of the opposed jaws of the RF ablation clamp of FIG. 1 taken along line 4-4 of FIG. 3.

FIGS. 5-7 illustrate the creation of overlapping energy fields between two pairs of spaced apart electrodes by alternately energizing the electrodes of each pair in accordance with the method of the present invention.

FIGS. 8-10 sequentially illustrate the formation of a lesion in tissue held between opposed jaw members having two pairs of opposed electrodes in accordance with practicing the method of the present invention.

DETAILED DESCRIPTION OF THE INVENTION

Figures 11, 12, 13:
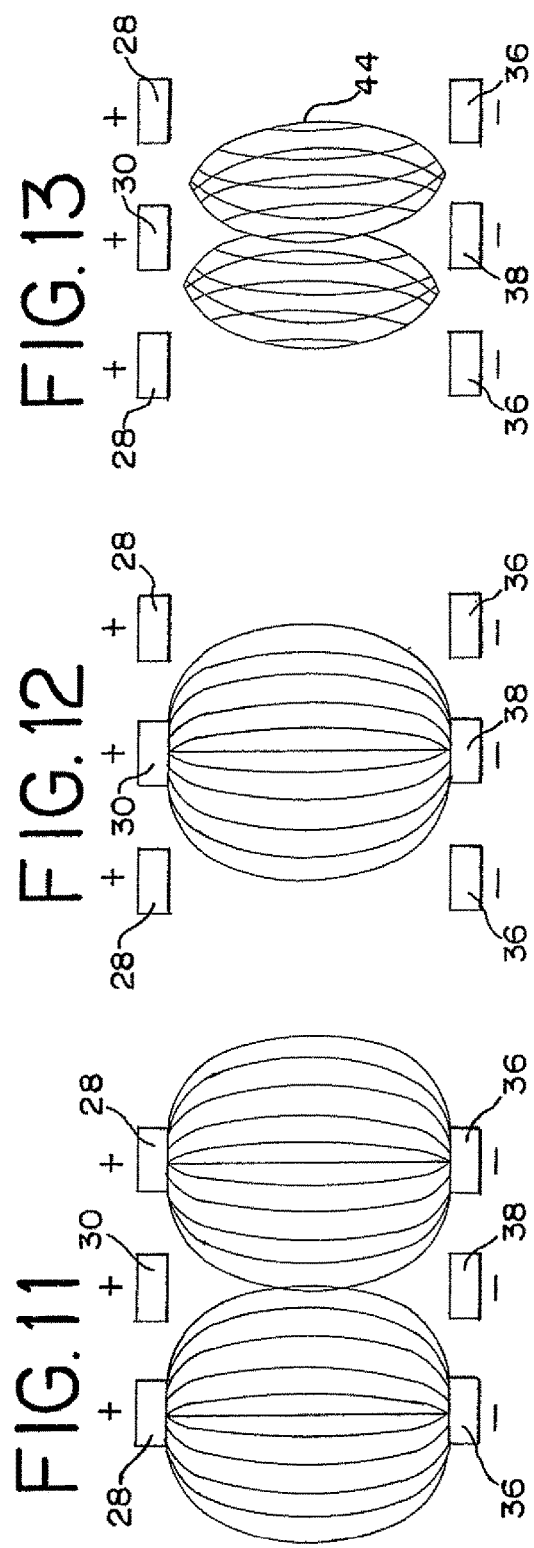
FIGS. 11-13 illustrate the creation of overlapping energy fields when three pairs of opposed electrodes are used in accordance with the method of the present invention.

The following description of certain examples of the invention is not intended and should not be used to limit the scope of the present invention. Other examples, features, aspects, embodiments, and advantages of the invention will become apparent to those skilled in the art from the following description, which is by way of illustration of one or more of the best modes contemplated for carrying out the invention. As will be realized, the invention is capable of other different and obvious aspects, all without departing from the invention. Accordingly, the drawings and descriptions should be regarded as illustrative in nature and not restrictive.

As described above, radio frequency (RF) energy can be used in electrosurgical systems for heating, coagulation, or ablating tissue. Monopolar and bipolar RF systems are known to those skilled in the art, and it is well known to use a bipolar electrosurgical clamping device. Bipolar electrosurgical instruments apply energy between a pair of electrodes in direct contact with the tissue to be ablated and provide more precise control of the extent of ablation than monopolar energy. It is well known to use a bipolar electrosurgical a clamping device with a pair of opposed RF electrodes to clamp and ablate tissue therebetween, and the ablated tissue may produce a generally continuous lesion which can be well suited for the treatment of cardiac arrhythmias. The Atricure Isolator® and ASU from Atricure, Inc. of Cincinnati, Ohio, is system useful for such treatment of atrial fibrillation.

In accordance with one aspect of the present invention, FIG. 1 illustrates an example of a tissue ablation system in the form of a bipolar electrosurgical system 10 having an electrosurgical instrument 12 coupled to an energy generator, e.g., an RF generator 14. Electrosurgical instrument 10 preferably comprises a handle 16, an elongated longitudinal shaft 17 extending therefrom, and an end effector 18 for clamping and heating tissue therebetween. Although illustrated as a clamping device particularly suited for open procedures where the ablation site is directly viewable by the surgeon, the present invention is also well suited for minimally invasive procedures, such as intercostal or subxyphoid approaches to cardiac tissue targeted for ablation.

The illustrated end effector 18 has first and second opposed jaws for clamping tissue therebetween, henceforth referred to for convenience as proximal jaw 20 and distal jaw 22. The proximal and distal jaws 20, 22 are shown spaced apart for the reception of tissue therebetween, but at least one of the proximal and distal jaws 20, 22 respectively could be movable to clamp tissue therebetween. To this end, proximal and distal jaws 20, 22 may be operably coupled to a closure trigger 24 extending proximally from the handle 16 such that it is operable with one hand so that distal movement of closure trigger 24 brings the proximal and distal jaws 20, 22 together. Likewise, proximal movement of closure trigger 24 moves the proximal and distal jaws 50, 55 apart. The proximal and distal jaws 20, 22 are shown extending at an angle from the shaft 16, but can be at any angle with the shaft 17. The present invention is not limited to the particular mechanism for moving the jaw(s) and an example of such a mechanism may be found in U.S. Pat. No. 6,923,806 and U.S. application Ser. No. 10/263,386, filed Oct. 2, 2002, both of which are incorporated by reference herein.

The invention provides for a method, apparatus and system for ablating tissue that comprises positioning two or more preferably bidirectional ablation energy sources in spaced-apart relation in sufficient proximity to the tissue to be ablated so that, upon activation each energy source creates an energy field in the tissue to be ablated. The energy sources are spaced such that the energy fields created by at least one of the activated sources partially overlaps with the energy field created by one or more of the other energy sources. The energy sources are alternately activated and deactivated, so that a substantially constant energy field results where the energy fields created by at least two of the energy sources overlap. While the energy sources are preferably RF energy sources, other energy sources, such as microwave, may be used.

To that end, and in keeping with one aspect of the invention that employs RF energy, two or more pairs of opposed electrodes are located in proximal and distal jaws 20, 22 of the instrument 12. All of the electrodes are operably coupled to the RF generator 14 by a cable 26 and can be operator actuated by a switch, such as a foot switch extending therefrom. A control system/RF generator for providing RF energy and for use in the system of the present invention is shown in the application U.S. Ser. No. 60/884,783, filed Jan. 12, 2006 in the name of Chris Park et al. entitled Matrix Router with Frequency Switching, and in U.S. Ser. No. 11/457,531, filed Jul. 14, 2006, which claims the benefit of U.S. Ser. No. 60/699,664, filed Jul. 15, 2005, all of which are incorporated herein by reference.

The RF energy monitored impedance delivered to the electrode pairs is preferably based, at least in part, on the monitored impedance of the tissue to be ablated as it is held between the jaws of the instrument. To this end, the controller preferably monitors or senses voltage and/or currents associated therewith, calculating or deriving the impedance of the tissue between the electrodes of at least one of the pairs of opposed electrodes and preferably between at least two of the pairs of opposed electrodes. The ablation may continue until the calculated impedance indicates that the lesion or ablation line is transmural (or fully through the tissue thickness).

With reference to in FIGS. 2-4, an electrosurgical instrument 12 according to the present invention having two pairs of opposed electrodes is shown. The proximal jaw 20 has a first electrode 28 and a second electrode 30 in a proximal insulator 32 that extends along the length and across the width of the jaw. The electrodes 28, 30 are preferably centered laterally on the insulator 32 about the medial plane of the jaw and spaced apart a distance 34 of from about 0.7 mm to 4 mm, the distance being a factor of the thickness of the tissue to be ablated. Other factors influencing the distance 34 between the electrodes include the type of tissue (e.g. cardiac, skeletal muscle or smooth muscle, such as the small bowel or uterus wall), the frequency of energy source switching, the desired duration of ablation, and the desired width of ablation. If the tissue to be ablated is about 5 mm thick (uncompressed), which is typical of cardiac tissue, the preferred electrode spacing is approximately 1.0 mm. As the spacing of the electrodes is increased, it is preferred that the insulator surface be convex so that the desired increased pressure on the tissue between the electrodes is achieved. With two pairs of opposed electrodes, the crown radius of the insulator of a preferred embodiment is about 4.5 mm, and its face width is about 5 mm. These dimensions are illustrative only, and other dimensions may be used without departing from the present invention in its broader respects.

The distal jaw 22 is configured similarly to the proximal jaw 20 and has a third electrode 36 preferably directly opposite to first electrode 28 and a fourth electrode 38 preferably directly opposite to second electrode 30. Electrodes 36, 38 are mounted in a distal insulator 40 with an electrode spacing 42, preferably matching the spacing in the proximal jaw so that the electrodes in each pair are in opposed relation. Electrodes 28, 30, 36, 38 are preferably identical in size and shape and preferably have a beryllium-copper base with a nickel/gold plating covering all exposed surfaces. The electrodes have a preferred electrode width 44 of about 0.012 inches and extend from the surface of the insulator over the length of the ablation surface from about 0.000 mm to about 0.15 mm. Other widths and projections may also be used.

With reference to FIGS. 5-7, the four electrodes 28, 30, 36, 38 can form parallel dual electrode arrays that can be pulsed. That is, electrodes 28 and 36 define one ablation energy source in the form of one pair of opposed electrodes having opposite polarity and electrodes 30 and 38 define another energy source in the form of a second pair of opposed electrodes that have opposite polarity. Although in the drawings the electrodes on each jaw are indicated as being of the same polarity, the electrodes on each jaw may be of the same or opposite polarity without departing from the invention. When energized by the RF generator, electrical current flows between the electrodes, creating an energy field in the form of current flow or flux between the electrodes that generally, for purposes of illustration, is shown in FIGS. 5 and 6. As can be seen there, the current density is highest at the electrode surfaces, i.e. at the interface between the electrodes and the tissue, which, prior to the present invention, would also be expected to be the area of primary tissue heating. However, in accordance with one aspect of the present invention, the two energy sources or pairs of opposing electrodes can be pulsed by energizing the first electrode pair 28, 36 for a timed duration (FIG. 5), turning the first electrode pair 28, 36 off and energizing the second electrode pair 30, 38 for the another, preferably the same, timed duration (FIG. 6), turning the second electrode pair 30, 38 off and repeating the pulsing cycle (alternately energizing and de-energizing the first electrode pair 28, 36 and the second pair 30, 38), thus creating an area of overlapping current flux 44 (FIG. 7). The overlapping area of current flux is thus subjected to a substantially continuous current flow, while the other tissue, including tissue at the electrode interface, experiences only intermittent current flow. As a result, a zone of primary tissue heating is created in the area of overlap, which is spaced from the area of highest current density.

The cycling of the electrodes is preferably repeated until the ablation of the tissue is transmural. Thus, to achieve a transmural ablation line, the opposing pairs of electrodes are cycled in a series of on-off first pair, on-off second pair cycles until ablation is complete. It has been determined that transmural ablation is achieved when the temperature of the tissue reaches approximately 50° C. Thus, one or more temperature sensors may be associated with the jaws to provide an indication of the progress of ablation. The temperature sensor(s) may be located on one or both jaws between the electrodes forming part of each opposed pair or on the jaws outside of the electrodes to detect thermal spread, which is the lateral spread of heat from the area or zone of ablation into tissues outside the zone.

FIGS. 8-10 illustrate the proximal and distal jaws 20, 22 clamped on tissue 48 of a tissue thickness 50. The clamping pressure is pressing the jaws 20, 22 into the tissue to create a jaw gap 52 that is typically less than the tissue thickness 50. The clamping pressure may be controlled by a tissue pressure system, such as a lost motion means, located in the handle of the electrosurgical device in a manner known as the prior art. Note that the tissue is compressed between two arcuate surfaces formed from the electrodes 28, 30, 26, 38 and the proximal insulator 32 and the distal insulator 40. These arcuate surfaces preferably apply the highest tissue pressure across the narrowest clamp gap 52 and the electrodes 28, 30, 36, 36, 38 flank this high pressure region. The pressure exerted on the tissue to be ablated is preferably sufficient to reduce the moisture in the tissue held between the jaws. This pressure is proportional to the thickness of the tissue to be ablated, and is typically between about 10 and 23 psi for typical cardiac tissue having an uncompressed thickness of about 5 mm, with a preferred clamping pressure of about 16 psi. for cardiac tissue having a compressed thickness of about 2 mm.

As indicated above, by energizing the electrodes alternately, as shown in FIGS. 5-7, a zone of primary heating is created in tissue held therebetween where there is a continuous flux, that is where the fluxes overlap, as designated 44 in FIG. 7. A zone of primary heating results that is offset from the zones of highest current density, which is directly between the electrodes of each pair, as shown in FIGS. 5 and 6. The pulsing frequency is preferably between about 2 and 575 Hz, and more preferably between about 10 and 376 Hz, with a higher frequency being preferred for ablating thinner tissue structures and a lower frequency being preferred for thicker tissue structures. The alternate energizing or pulsing of the electrodes means that the electrodes energized only 50 percent of the time if the on-off cycles are identical. This half-duty cycle provides for balanced ablation and allows the electrode surfaces to be substantially cooler than if they were operated continuously. As a result, ablation 54 starts centrally in the tissue in the zone of primary heating, and gradually extends or expands outwardly toward the jaw surfaces, as shown in FIGS. 8-10. Because the ablation does not start at the electrode surface, the impedance at the electrode surface does not increase as rapidly as with a single pair of opposed electrodes, resulting in a more efficient ablation process. If desired, the duty-cycle could be something other than half-on, half-off, such as 60% on, 40% off, to achieve an ablation biased to one side or the other.

With reference to FIGS. 11-13, the present invention also contemplates using multiple energy sources, for example, three or more pairs of opposed electrodes, and alternately energizing the adjacent electrodes. With reference to FIGS. 11-13, for example, three pairs of opposed electrodes are schematically illustrated, with the outer two pairs being fired simultaneously (FIG. 11) and then being deactivated with the central electrode pair being fired (FIG. 12) to result in two zones of primary heating being created between the jaws corresponding to the two zones of overlapping current flux, both zones being spaced from the zones of highest current density that occurs directly between the electrodes of each pair and at the electrode-tissue interface. The number of electrode pairs utilized is selected based upon the desired width of the ablation line to be obtained. The number of electrode pairs may be more than three pairs, and may be an even or odd number of electrode pairs.

Figure 14:
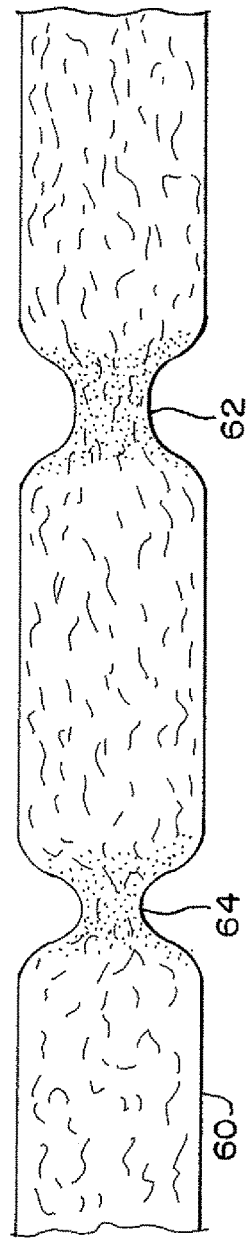
FIG. 14 is a cross-sectional view of tissue comparing the profile of the ablated tissue when the method according to the present invention is performed and that obtained by practicing the prior art.

With reference to FIG. 14, there is seen a representation in cross-section of tissue 60 ablated with a device having a single pair of opposed electrodes and with a device having two pairs of opposed electrodes operated according to the methods described above. The ablation line cross-section 62 resulting from the use of two pairs of electrodes is wider than the ablation line cross-section 64 resulting from a similarly configured instrument having a single pair of opposed electrodes, resulting in an ablation line that is more visible to the surgeon. However, the ablation line 62 continues to be maintained within the width of the jaws and forms a relatively well-defined line of ablation with limited lateral extent and limited thermal spread to adjacent tissue. Thus, the device of the present invention provides for wider ablation lines that are well defined and do not spread beyond the width of the jaws. Ablations obtained by use of the present invention are also wider at the core than those using a single pair of opposed electrodes, and have more of a barrel shape than an hour-glass shape as shown in the drawing.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

While the present invention has been illustrated by description of several embodiments and while the illustrative embodiments have been described in considerable detail, it is not the intention of the applicant to restrict or in any way limit the scope of the appended claims to such detail. For example, while the invention has been described as using bipolar RF energy, other energy sources may be used, such as microwave energy. Additional advantages and modifications may readily appear to those skilled in the art.

The invention claimed is:

1. A tissue ablation system comprising:
an energy generator;
a plurality of ablation energy sources adapted to be positioned in proximity to tissue to be ablated, each energy source being in operative communication with the generator, each source when activated generating an energy field, the sources being relatively positioned so that the energy fields of the sources partially overlap;
a control system operatively associated with the generator and sources, and configured to alternately activate and deactivate the sources so that a substantially constant energy field is created in the area of overlap.

2. The system of claim 1 including a monitor operable to monitor ablation of the tissue.

3. The system of claim 1 including a pair of opposed relatively movable surfaces adapted to apply pressure to the tissue during ablation thereof.

4. The system of claim 3 wherein the opposed surfaces are adapted to apply pressure sufficient to reduce the moisture content of the tissue during ablation.

5. The system of claim 4 wherein the tissue has a thickness and the pressure is proportional to the thickness of the tissue.

6. The system of claim 3 in which the opposed, relatively movable surfaces are adapted to apply pressure between about 10 and 23 psi to the tissue to be ablated, the tissue having an uncompressed thickness of about 5 mm.

7. The system of claim 6 in which the opposed movable surfaces are adapted to apply pressure of about 16 psi to tissue having a compressed thickness of about 2 mm.

8. The system of claim 3 wherein the energy sources are carried on at least one of the opposed surfaces.

9. The system of claim 1 wherein each energy source comprises an RF energy source.

10. The system of claim 1 wherein each energy source comprises at least two electrodes, the two electrodes of each energy source comprising a bi-polar electrode configuration.

11. The system of claim 10 in which the electrodes are alternately activated and deactivated at a frequency of between about 2 and 575 Hz.

12. The system of claim 10 further including an impedance monitor operable to monitor impedance between the electrodes of at least one of the energy sources.

13. The system of claim 10 further including an impedance monitor operable to monitor impedance between at least two of the energy sources.

14. The system of claim 10 in which the electrodes are alternately activated and deactivated at a frequency of between about 10 and 376 Hz.

15. The system of claim 1 wherein the plurality of ablation energy sources are operable to create a plurality of areas of overlapping energy fields.

16. The system of claim 1 wherein the density of the energy field is less in the area of overlap than closer to the energy source.

17. The system of claim 1 further comprising a temperature sensor positioned to sense the temperature of tissue.

18. The system of claim 17 in which the temperature sensor is disposed to sense the temperature of tissue between the energy sources.

19. The system of claim 17 in which the temperature sensor is disposed to sense the temperature of tissue outside the energy sources.

20. The system of claim 1 where the number of energy sources is at least three, one of the energy sources being positioned between at least two other energy sources, wherein the control system is configured to activate said at least two other energy sources substantially simultaneously, and is configured to alternately activate and deactivate said one of the energy sources with the other two energy sources.

21. Tissue ablation apparatus comprising:
    opposed relatively movable jaws for engaging tissue to be ablated therebetween;
    a plurality of electrode pairs, one electrode of each pair being carried on one jaw and being adapted to be connected to one terminal of an RF generator and the other electrode of each pair being carried on the other jaw and being adapted to be connected to the opposite terminal of an RF generator to create a current flux between the respective electrodes of each pair when activated by the generator;
    the plurality of electrode pairs being located on the jaws;
    a control system operatively associated with the plurality of electrode pairs and configured to alternately activate and deactivate the plurality of electrode pairs to create at least one flux zone of primary heating in the tissue spaced from at least one flux zone of highest current flux in the tissue.

22. The apparatus of claim 21 comprising three or more electrode pairs positioned to create a plurality of flux zones of primary heating.

23. The apparatus of claim 21 wherein the jaws are adapted to exert sufficient pressure on the clamped tissue to reduce the moisture content of the tissue.

24. The apparatus of claim 23 wherein the tissue has a thickness and the pressure is proportional to the thickness of the tissue.

25. The apparatus of claim 23 wherein the jaws are adapted to exert sufficient pressure on the clamped tissue and in which the pressure is between about 10 and 23 psi for tissue having an uncompressed thickness of about 5 mm.

26. The apparatus of claim 25 in which the pressure is about 16 psi on tissue having a compressed thickness of about 2 mm.

27. The apparatus of claim 23 in which the pressure applied to the tissue is greater at a location between the electrode pairs than between the electrodes of each electrode pair.

28. The apparatus of claim 21 including a sensor carried by one of the jaws for sensing the temperature of the tissue at a selected location.

29. The apparatus of claim 28 wherein the sensor is positioned to sense the temperature of tissue between electrode pairs.

30. The apparatus of claim 28 wherein the sensor is positioned to sense the temperature of tissue outside the electrode pairs.

31. The apparatus of claim 28 in which the insulating surface between the electrodes is generally convex.

32. The apparatus of claim 21 wherein the electrodes on each jaw are spaced from about 0.7 mm to about 4.0 mm apart.

33. The apparatus of claim 21 wherein the electrodes of each electrode pair are elongated and the distance between adjacent electrodes on a given jaw is substantially constant.

34. The apparatus of claim 21 wherein each jaw member has an insulating surface facing the opposing jaw and the electrodes of each jaw extend from about 0.00 mm to about 0.15 mm above the insulating surface.

35. The apparatus of claim 21 wherein each jaw member has an insulating surface facing the opposing jaw and the electrodes extend from and are interposed by the insulating surface, and the insulating surface between electrodes extends toward the opposing jaw to cause greater compression of clamped tissue between the electrodes than adjacent the electrodes.

* * * * *